(12) United States Patent
Kwon et al.

(10) Patent No.: US 9,993,176 B2
(45) Date of Patent: Jun. 12, 2018

(54) APPARATUS AND METHOD FOR DETECTING BIOSIGNAL

(71) Applicant: Samsung Electronics Co., Ltd., Suwon-si (KR)

(72) Inventors: Ui Kun Kwon, Hwaseong-si (KR); Sang Joon Kim, Hwaseong-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 66 days.

(21) Appl. No.: 14/661,263

(22) Filed: Mar. 18, 2015

(65) Prior Publication Data

US 2016/0066845 A1 Mar. 10, 2016

(30) Foreign Application Priority Data

Sep. 5, 2014 (KR) .................. 10-2014-0118903

(51) Int. Cl.
*A61B 5/053* (2006.01)
*A61B 5/00* (2006.01)

(52) U.S. Cl.
CPC .......... *A61B 5/0531* (2013.01); *A61B 5/6802* (2013.01); *A61B 5/6826* (2013.01); *A61B 2560/0276* (2013.01); *A61B 2560/0468* (2013.01)

(58) Field of Classification Search
CPC . A61B 5/0404; A61B 5/04085; A61B 5/0492; A61B 5/0531; A61B 5/6826
USPC ........................................................ 600/384
See application file for complete search history.

(56) References Cited

U.S. PATENT DOCUMENTS

| | | | | |
|---|---|---|---|---|
| 5,974,262 A | * | 10/1999 | Fuller | G06F 3/015 600/301 |
| 6,608,562 B1 | * | 8/2003 | Kimura | A61B 5/02427 128/903 |
| 6,950,695 B2 | * | 9/2005 | Chen | A61B 5/02438 600/509 |
| 7,161,484 B2 | * | 1/2007 | Tsoukalis | A61B 5/0002 340/539.1 |
| 9,311,825 B2 | * | 4/2016 | Lusted | G09B 19/00 |
| 2004/0015094 A1 | * | 1/2004 | Manabe | A61B 5/0492 600/546 |
| 2011/0245633 A1 | * | 10/2011 | Goldberg | A61B 5/681 600/301 |
| 2015/0164422 A1 | * | 6/2015 | Lee | A61B 5/6831 600/301 |
| 2015/0182129 A1 | * | 7/2015 | Colley | A61B 5/0205 600/301 |

FOREIGN PATENT DOCUMENTS

| | | | |
|---|---|---|---|
| JP | 10-71268 A | | 3/1998 |
| JP | 11-332840 A | | 12/1999 |
| JP | 2006-61466 | * | 3/2006 |
| JP | 4607709 B2 | | 10/2010 |
| JP | 4683148 B2 | | 2/2011 |

(Continued)

*Primary Examiner* — Lee S Cohen
(74) *Attorney, Agent, or Firm* — NSIP Law

(57) ABSTRACT

A biosignal detecting apparatus and method thereof are disclosed, including a ring-type main body, and a pair of electrodes configured to be in contact with a finger of a user and to detect a biosignal of the user. An electrode of the pair of electrodes is disposed along an inner surface of the main body.

12 Claims, 13 Drawing Sheets

(56) References Cited

FOREIGN PATENT DOCUMENTS

| KR | 10-2011-0002373 A | | 1/2011 |
|---|---|---|---|
| KR | 10-1042827 B1 | | 6/2011 |
| KR | 10-1324560 B1 | | 10/2013 |
| WO | WO2015196298 | * | 12/2015 |
| WO | WO2016123216 | * | 8/2016 |
| WO | WO2016134170 | * | 8/2016 |

* cited by examiner

APPARATUS AND METHOD FOR DETECTING BIOSIGNAL

CROSS-REFERENCE TO RELATED APPLICATION

This application claims the benefit under 35 USC 119(a) of Korean Patent Application No. 10-2014-0118903, filed on Sep. 5, 2014, in the Korean Intellectual Property Office, the entire disclosure of which is incorporated herein by reference for all purposes.

BACKGROUND

1. Field

The following description relates to an apparatus and a method to detect a biosignal.

2. Description of Related Art

Human emotions may be measured by a device using face or voice recognition. In addition to the recognition, research has been conducted on a method to extract an emotion based on a biosignal. For example, an emotion is measured based on an electrical conductance of skin or a skin conductance. A general application of such skin conductance includes a lie detector and a concentration measurer.

For example, the skin conductance is measured at a wrist of a user. When the skin conductance is measured at the wrist, a sensitivity to sympathetic nerves may decrease and; thus, an accuracy in measuring the skin conductance may decrease.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In accordance with an aspect, there is provided a biosignal detecting apparatus, including a ring-type main body; and a pair of electrodes configured to be in contact with a finger of a user and to detect a biosignal of the user, wherein an electrode of the pair of electrodes is disposed along an inner surface of the main body.

The apparatus may also include a reference unit disposed on an outer surface of the main body to allow a reference position of the biosignal detecting apparatus to be identified.

The reference unit may include an ornament.

The electrode of the pair of electrodes may be disposed along one surface of the inner surface between the reference position and another reference position, opposite to the reference position, and another electrode of the pair of electrodes may be disposed along another surface of the inner surface between the reference position and the another reference position.

The pair of the electrodes may be alternately disposed along the inner surface.

The electrode of the pair of electrodes may be disposed along the inner surface, and another electrode of the pair of electrodes is disposed along an outer surface.

The inner surface may be divided into two surfaces by a baseline formed along the inner surface, and the electrode of the pair of electrodes may be disposed along one surface of the two surfaces, and another electrode of the pair of electrodes is disposed along another surface of the two surfaces.

The apparatus may include an outputter configured to output information on the detected biosignal.

The apparatus may also include a communicator configured to transmit information about the detected biosignal.

The biosignal may be an electrical conductance of skin.

The electrodes may be spaced apart within the inner surface of the main body.

The apparatus may also include a processor configured to verify whether a measured value of a biosignal detected is in a reference range; a communication module configured to transmit information about the biosignal detected to a user terminal in response to the measured value being verified; and an outputter configured to display the information about the biosignal detected.

When the measured value is not within the reference range, the processor controls the biosignal detecting apparatus to apply a physical stimulus to a user.

In accordance with an aspect, there is provided a biosignal detecting apparatus, including a pair of electrodes; a ring-type first body in which one electrode of the pair of electrodes is disposed; and a ring-type second body in which another electrode of the pair of electrodes is disposed, wherein the pair of the electrodes is configured to detect a biosignal based on a contact between the first body and the second body.

The apparatus may also include an outputter configured to output information about the detected biosignal.

The apparatus may also include a communicator configured to transmit information on the detected biosignal.

The biosignal may be an electrical conductance of skin.

In accordance with an aspect, there is provided a method of a biosignal detecting apparatus, the method includes configuring an electrode of a pair of electrodes to be disposed along an inner surface of a main body of the biosignal detecting apparatus; and detecting a biosignal of a user from a contact between the pair of electrodes and a finger of the user.

The method may also include identifying a reference position of the biosignal detecting apparatus along an outer surface of the main body.

The method may also include arranging a ring-type auxiliary body physically separately from the main body; disposing the electrode of the pair of electrodes along the inner surface of the main body; and disposing another electrode of the pair of electrodes along an inner surface of the auxiliary body, wherein the detecting of the biosignal comprises detecting the biosignal based on an electrical contact between the main body and the auxiliary body.

Other features and aspects will be apparent from the following detailed description, the drawings, and the claims.

BRIEF DESCRIPTION OF THE DRAWINGS

These and/or other aspects will become apparent and more readily appreciated from the following description of the embodiments, taken in conjunction with the accompanying drawings in which.

Figure 1:
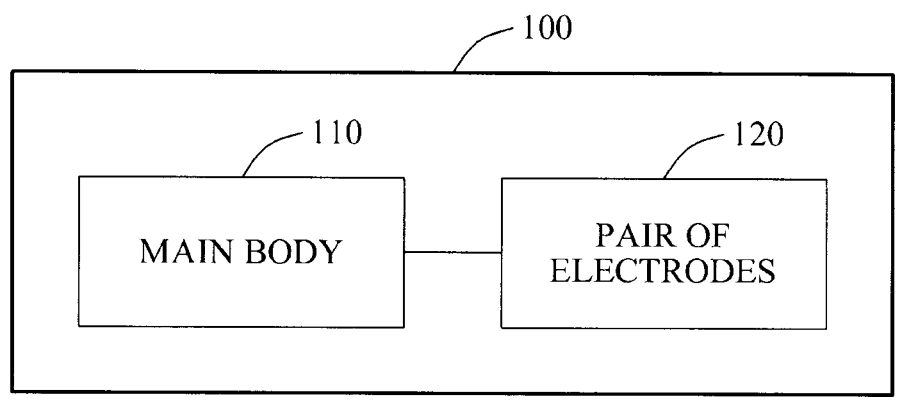
FIG. 1 is a diagram illustrating an example of a configuration of a biosignal detecting apparatus, in accordance with an embodiment.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the systems, apparatuses and/or methods described herein will be apparent to one of ordinary skill in the art. Also, descriptions of functions and constructions that are well known to one of ordinary skill in the art may be omitted for increased clarity and conciseness.

Throughout the drawings and the detailed description, the same reference numerals refer to the same elements. The drawings may not be to scale, and the relative size, proportions, and depiction of elements in the drawings may be exaggerated for clarity, illustration, and convenience.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

Example embodiments will now be described more fully with reference to the accompanying drawings in which example embodiments are shown. Example embodiments, may, however, be embodied in many different forms and should not be construed as being limited to the embodiments set forth herein; rather, these example embodiments are provided so that this disclosure will be thorough and complete, and will fully convey the scope of example embodiments to those of ordinary skill in the art. In the drawings, the thicknesses of layers and areas are exaggerated for clarity. Like reference numerals in the drawings denote like elements, and thus their description may be omitted.

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Expressions such as "at least one of," when preceding a list of elements, modify the entire list of elements and do not modify the individual elements of the list.

Unless otherwise defined, all terms (including technical and scientific terms) used herein have the same meaning as commonly understood by one of ordinary skill in the art to which example embodiments belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

FIG. 1 is a diagram illustrating an example of a configuration of a biosignal detecting apparatus 100, in accordance with an embodiment.

Referring to FIG. 1, the biosignal detecting apparatus 100 includes a main body 110 and at least one pair 120 of electrodes.

In one illustrative example, the main body 110 is provided in a form of a ring. That is, the main body 110 is provided in a shape of a ring to be worn around a finger of a user. A width of the ring of the main body 110 may vary from one millimeter to 20 millimeters. In another configuration, the ring may be configured to substantially, more than 20 millimeters, to an entire finger of a user.

The at least one pair 120 of the electrodes is in contact with the finger of the user to detect a biosignal of the user. At least one electrode of the electrodes included in the at least one pair 120 is disposed in an inner surface of the main body 110 to be in contact or in direct contact with the finger.

The biosignal detecting apparatus 100 measures an electrical conductance of skin, hereinafter referred to as a "skin conductance," of the user's finger using the at least one pair 120 of the electrodes. The skin conductance is obtained based on a resistance or an impedance between two points of the skin. A human nervous system is divided into a central nervous system and an automatic nervous system. The automatic nervous system is activated irrespective of an intention of a human being. When sympathetic nerves in the automatic nervous system are activated, perspiration occurs in a portion of a body. Sweat glands responsive to the sympathetic nerves are distributed mainly in a forehead, a finger, a palm of a hand, and a sole of a foot. Thus, measuring a skin conductance of the finger, a palm, or a sole of the user may facilitate an observation of a response of the sympathetic nerves.

The biosignal detecting apparatus 100 measures a resistance between electrodes occurring by the response of the sympathetic nerves. The resistance to be measured includes a resistance of an electrode, a resistance between skin and the electrode, and a resistance of a body of the user.

The at least one pair 120 includes a dry electrode. The dry electrode includes a conductive material, for example, a metal, and is in contact with the skin.

The biosignal detecting apparatus 100 further includes a reference unit, to be later described and illustrated in FIG. 2, disposed on an outer surface of the main body 110 to allow a reference position of the biosignal detecting apparatus 100 to be identified. For example, in use, the biosignal detecting apparatus 100 worn around the finger of the user moves or displaces on the finger, without necessarily being fixed at a wearing position. When such a movement occurs, a size of a contact surface on which an electrode and the skin is in contact with each other may change. Based on the change in the size of the contact surface, a value of the biosignal to be measured may change. Also, the user may adjust the wearing position at which the biosignal detecting apparatus 100 is worn relative to the reference unit. The reference unit may include an ornament, such as a stone or a charm.

In one configuration, the electrodes included in the at least one pair 120 are arranged in a form of a half ring. A further description will be provided with reference to FIG. 2. In another configuration, depending on the width of the ring, the electrodes may be discrete structural elements linearly arranged, arranged in a matrix pattern, or arranged in a random pattern along a portion or an entire inner surface of the ring.

Figure 2:
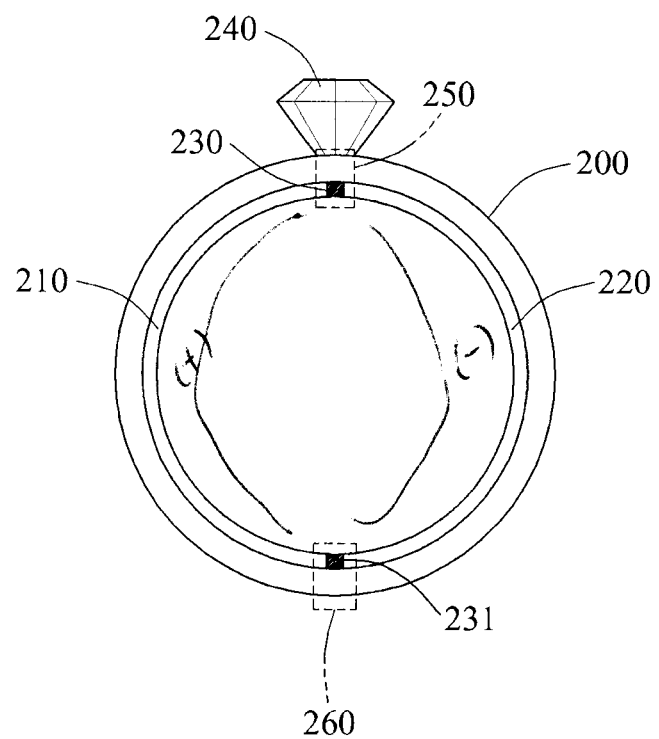
FIGS. 2, 3, 4A, 4B, 4C, and 5 are diagrams illustrating examples of a pair of electrodes of the biosignal detecting apparatus, in accordance with an embodiment.

FIG. 2 is a diagram illustrating an example of a pair of electrodes of the biosignal detecting apparatus 200, in accordance with an embodiment.

Referring to FIG. 2, at least one pair of electrodes is disposed in an inner surface of a main body. An interval is present between a first electrode and a second electrode disposed in the inner surface. Positions, at which the first electrode and the second electrode are physically separated, are referred to as reference positions, for example, 230 and 231, of the biosignal detecting apparatus 200. A reference unit 240 is disposed on an outer surface of the main body corresponding to at least one of the reference positions 230 and 231. As previously indicated, the reference unit 240 is, in one example, an ornament to the main body. As illustrated in FIG. 2, the reference unit 240 is disposed on the outer surface corresponding to the reference position 230. The reference position 231 opposite to the outer surface on which the reference unit 240 is not disposed is referred to as an opposite reference position 231.

In an alternative configuration, an area or a location of the outer surface of the main body on which the reference unit 240 is disposed and an inner surface corresponding to the area or a location on which the reference unit 240 is disposed is a reference position 250. An opposite reference position 260 may correspond to the reference position 250. The opposite reference position 260 is located opposite to the reference position 250.

An electrode included in the at least one pair of the electrodes is disposed along the inner surface between the reference position 230 or 250 and the opposite reference position 231 or 260. For example, as illustrated in FIG. 2, a positive (+) electrode is disposed along one surface 210 of the inner surface between the reference position 230 or 250 and the opposite reference position 231 or 260. In one embodiment, the positive electrode covers the surface 210. Similarly, a negative (−) electrode is disposed along another surface 220 of the inner surface between the reference position 230 or 250 and the opposite reference position 231 or 260. The negative electrode covers the surface 220.

When a user wears the biosignal detecting apparatus 200, a measured value of a biosignal changes depending on a wearing position at which the biosignal detecting apparatus 200 is worn. The biosignal is measured more accurately on a palm of a hand than a dorsum of the hand. Based on the wearing position, a contact area between an electrode and the palm differs from a contact area between the electrode and the dorsum. Thus, due to a difference between the contact areas, a value of the biosignal to be measured varies depending on the wearing position. The user identifies the reference position of the biosignal detecting apparatus 200 using the reference unit 240. The user adjusts the wearing position of the biosignal detecting apparatus 200 to minimize a difference between a contact area between an electrode and a palmar side of a finger and a contact area between the electrode and a dorsal side of the finger.

The biosignal detecting apparatus 200 includes an interface, for example, 230 and 231, to prevent an electrical connection between the electrodes. The interface 230 and 231 is disposed between the electrodes and include an insulating material.

Referring back to FIG. 1, the at least one pair 120 of the electrodes are alternately disposed in the inner surface of the main body 110. A further description will be provided with reference to FIG. 3.

Figure 3:
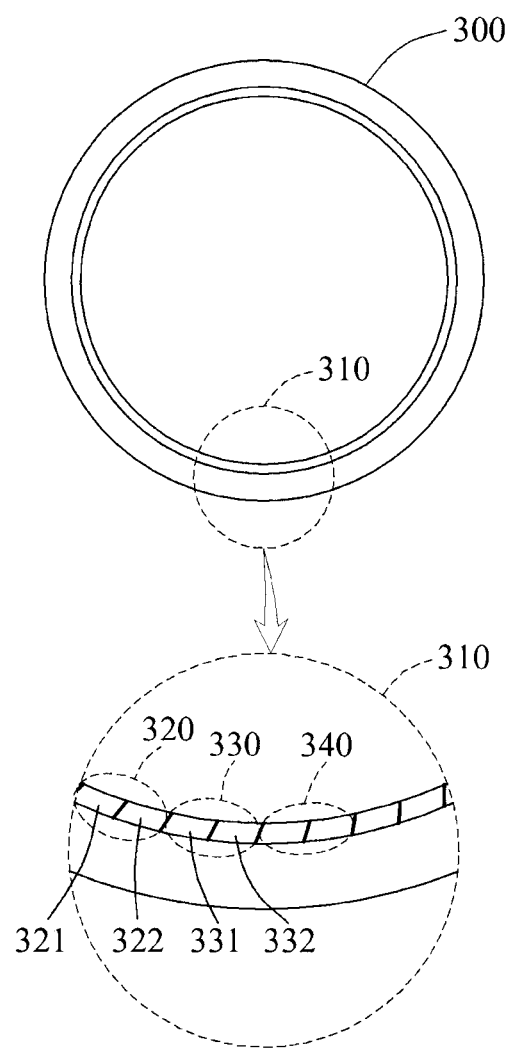

FIG. 3 is a diagram illustrating an example of a pair of electrodes of a biosignal detecting apparatus 300, in accordance with an embodiment.

Referring to FIG. 3, the pair of the electrodes is disposed in an inner surface of a main body. Pairs of electrodes, for example, 320, 330, and 340, are disposed adjacent to one another in an area 310 including the inner surface and an outer surface of the main body. The pairs of electrodes 320, 330, and 340 cover the inner surface. Interfaces may be disposed among the pairs of electrodes 320, 330, and 340 to prevent an electrical connection thereamong.

As illustrated in FIG. 3, an interface is disposed between an electrode 321 and an electrode 322 to prevent an electrical connection therebetween. Similarly, an interface is disposed between an electrode 331 and an electrode 332 to prevent an electrical connection therebetween. In the example of FIG. 3, a positive electrode and a negative electrode are alternately disposed along the inner surface.

In addition, the electrode 321 and the electrode 331 are electrically connected, and the electrode 322 and the electrode 332 are electrically connected. For example, positive electrodes disposed in the inner surface of the main body are electrically connected, and negative electrodes are electrically connected.

Referring back to FIG. 1, one electrode included in the at least one pair 120 of the electrodes is disposed along the inner surface of the main body 110. Another electrode included in the at least one pair 120 is disposed in the outer surface of the main body 110. A further description will be provided with reference to FIGS. 4A through 4C.

Figure 4A:
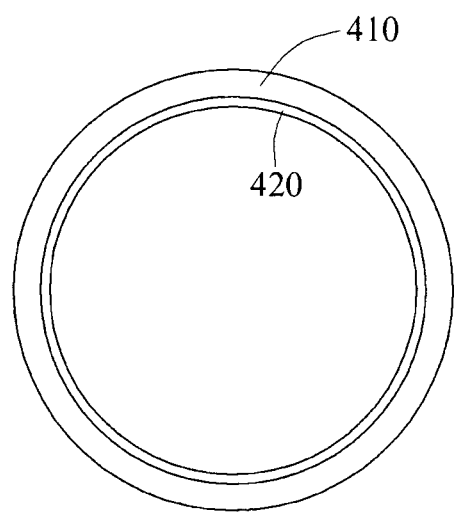
Figure 4B:
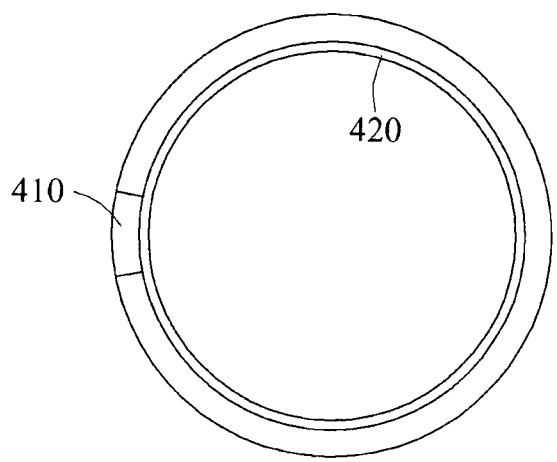
Figure 4C:
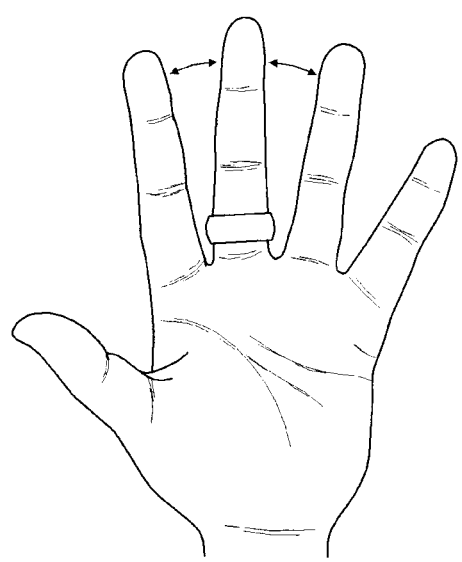

FIGS. 4A through 4C are diagrams illustrating an example of a pair of electrodes of a biosignal detecting apparatus.

Referring to FIGS. 4A through 4C, an electrode 420 included in the pair of the electrodes is disposed along an inner surface of a main body, and an electrode 410 is disposed along an outer surface of the main body.

Referring to FIG. 4A, the electrode 420 included in the pair of the electrodes is disposed along the inner surface of the main body, and the electrode 410 is disposed along the outer surface of the main body. In one configuration, a positive electrode of the pair is disposed along the inner surface, and a negative electrode of the pair is disposed along the outer surface. In an alternative configuration, the negative electrode is disposed along the inner surface, and the positive electrode is disposed along the outer surface.

An electrode included in the pair is provided in a form of a ring to be disposed along the inner surface and the outer surface thereof. A shape of the electrode may be identical to a shape of the main body.

Referring to FIG. 4B, the electrode 420 included in the pair is disposed along the inner surface of the main body. The electrode 410 included in the pair is disposed on one area or portion of the outer surface of the main body. In this example, the electrode 410 is not a ring-type electrode.

A method of using the biosignal detecting apparatus illustrated in FIGS. 4A and 4B will be described with reference to FIG. 4C. Referring to FIG. 4C, a user wears the biosignal detecting apparatus around a middle finger of the user. One electrode of the pair of the electrodes is disposed along an inner surface of the biosignal detecting apparatus worn around the middle finger. The electrode disposed along the inner surface of the biosignal detecting apparatus is disposed along a circumference of the inner surface. Another electrode included in the pair is disposed along an outer surface of the biosignal detecting apparatus. As illustrated as the electrode 410 in FIG. 4A, the electrode disposed along the outer surface of the biosignal detecting apparatus is disposed along the outer surface. Alternatively, as illustrated as the electrode 410 in FIG. 4B, the electrode is disposed in one area of the outer surface of the biosignal detecting apparatus.

The outer surface of the biosignal detecting apparatus is in contact with another finger in addition to the finger around which the biosignal detecting apparatus is worn. For example, the outer surface of the biosignal detecting apparatus is in contact with an index finger during movement of the fingers. In another example, the outer surface of the biosignal detecting apparatus is in contact with a ring finger during movement of the fingers. Thus, a closed loop is formed between two electrodes of the biosignal detecting apparatus and the user as a result of the contact between the outer surface of the biosignal detecting apparatus and another finger. Accordingly, the biosignal detecting apparatus detects a biosignal, for example, a skin conductance, based on the formation of the closed loop.

Referring back to FIG. 1, the at least one pair 120 of the electrodes is disposed along the inner surface of the main body 110. A further description will be provided with reference to FIG. 5.

Figure 5:
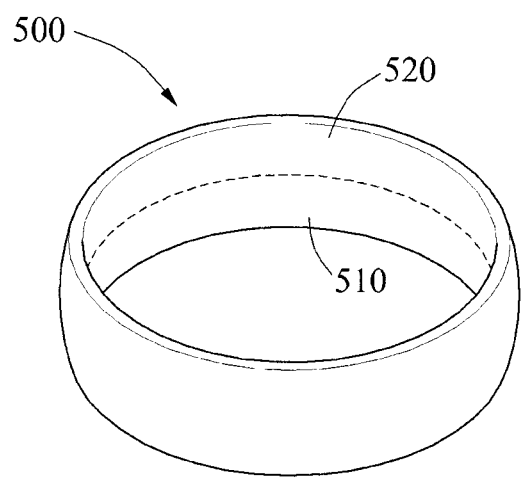

FIG. 5 is a diagram illustrating an example of a pair of electrodes of a biosignal detecting apparatus 500, in accordance with an embodiment.

Referring to FIG. 5, the pair of the electrodes is disposed along an inner surface of a main body. As illustrated in FIG. 5, one electrode included in the pair is disposed along one surface 510 of the inner surface, which is a lower portion from a dotted line or a mid-line indicated on the inner surface of the main body. Another electrode included in the pair is disposed along another surface 520 of the inner surface, which is an upper portion of the mid-line or with respect to the dotted line. An electrode is provided in a form of a ring to be disposed along the inner surface. An interface is disposed between the electrodes. The interface is disposed on the dotted line. The interface prevents an electrical connection between the electrodes. The interface includes an insulating material. The inner surface is divided into the surface 510 and the surface 520 based on the interface.

A baseline is formed along the inner surface of the main body to allow the electrodes included in the pair to be separately disposed. Based on the baseline, an electrode of the pair is disposed along the surface 510 of the inner surface, and an electrode of the pair is disposed along the surface 520 of the inner surface. The inner surface is divided into the surface 510 and the surface 520 based on the baseline.

Due to the pair of the electrodes disposed along the inner surface of the main body, a change in a contact area between an electrode and skin is minimized, or the contact area does not change, despite a movement of the biosignal detecting apparatus.

Referring back to FIG. 1, the biosignal detecting apparatus 100 further includes a processor, a communication module, and an outputter. The processor verifies whether a measured value of a biosignal detected by the biosignal detecting apparatus 100 is in a reference range. When the measured value is not in the reference range, the processor controls the biosignal detecting apparatus 100 to allow a physical stimulus to be applied to a user. For example, when the measured value is less than the reference range, the biosignal detecting apparatus 100 generates heat in an electrode in contact with the skin of the user. The skin of the user produces sweat due to the generation of the heat in the electrode and, as a result, the measured value of the biosignal is included in the reference range.

The communication module transmits information on the biosignal detected by the biosignal detecting apparatus 100 to a user terminal through wireless communication. In an alternative configuration, the communication module may be configured to be wire connectable to the user terminal or a server. For example, the communication module may include a Bluetooth device or a near field communication (NFC) module. The information about the biosignal is encoded for transmission.

The communication module outputs, through an outputter, the information about the biosignal detected by the biosignal detecting apparatus 100. For example, the outputter may include a display visually outputting the biosignal. The display may be provided in a form of a flexible display to be disposed on the outer surface of the main body 110. In addition, the outputter may output information indicating whether the biosignal detecting apparatus 100 detects a biosignal. For example, the outputter may include a light emitting diode (LED), and inform the user that the biosignal detecting apparatus 100 detects the biosignal using the LED.

Figure 6:
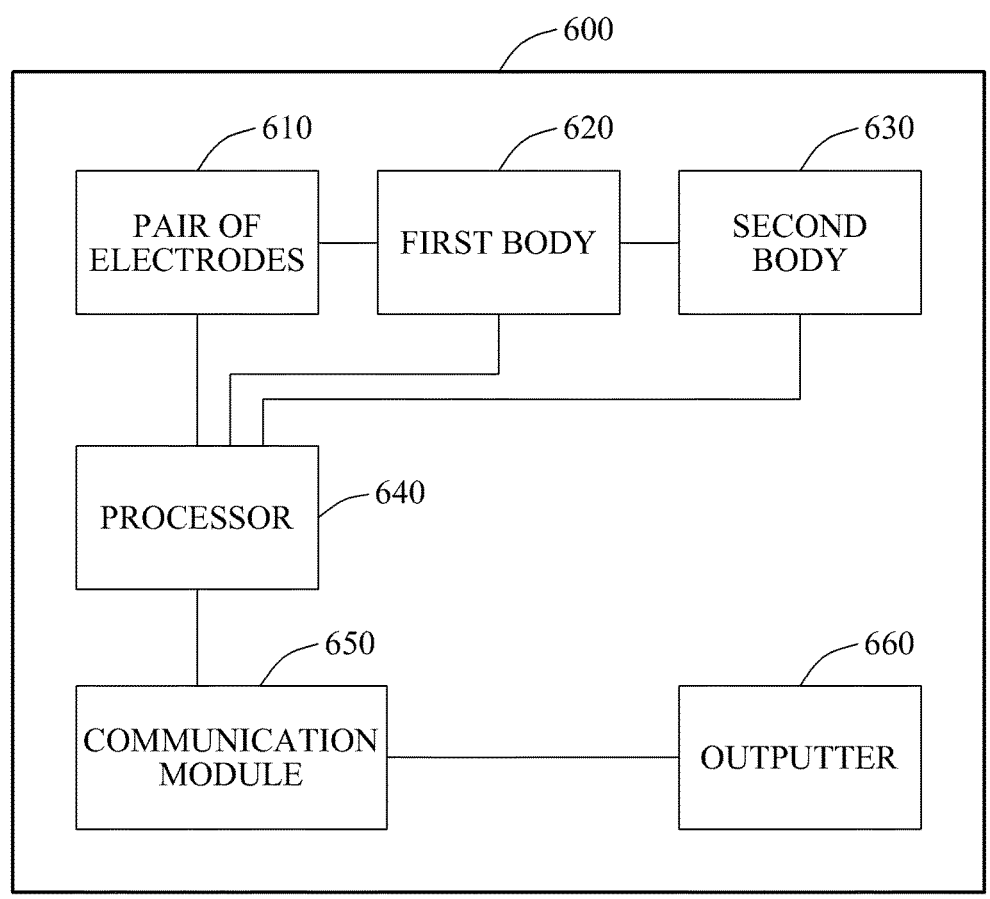
FIG. 6 is a diagram illustrating another example of a configuration of a biosignal detecting apparatus, in accordance with an embodiment.

FIG. 6 is a diagram illustrating another example of a biosignal detecting apparatus 600, in accordance with an embodiment.

Referring to FIG. 6, the biosignal detecting apparatus 600 includes at least one pair of electrodes 610, a first body 620, and a second body 630.

In one example, the first body 620 is provided in a shape of a ring, and one electrode included in the pair of electrodes 610 is disposed in an inner surface of the first body 620. For example, a positive electrode may be disposed along the inner surface of the first body 620. The positive electrode is provided in a shape identical to the first body 620 to be disposed along the inner surface.

The second body 630 is provided in a type of a ring, and another electrode included in the pair of electrodes 610 is disposed in an inner surface of the second body 630. For example, a negative electrode is disposed along the inner surface of the second body 630. The negative electrode is provided in a form identical to the second body 630 to be disposed along the inner surface.

An outer surface of the first body 620 and an outer surface of the second body 630 include a conductive material. When the outer surface of the first body 620 and the outer surface of the second body 630 are in contact, the pair of electrodes 610 detects a biosignal of a user. Conversely, when the outer surface of the first body 620 and the outer surface of the second body 630 are not in contact, the biosignal detecting apparatus 600 does not detect the biosignal of the user. A further description will be provided with reference to FIGS. 7 and 8.

Figure 7:
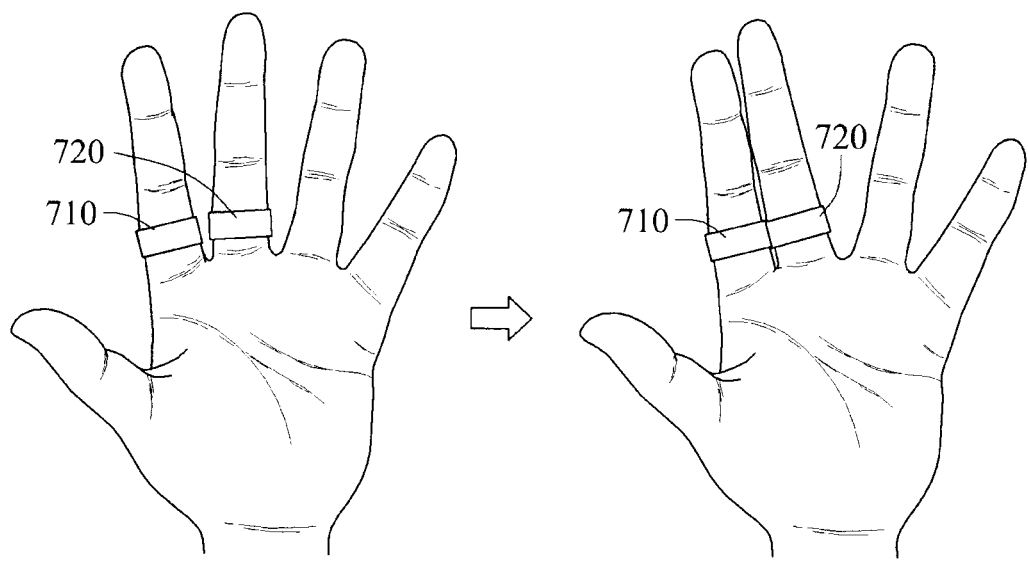
FIGS. 7 and 8 are diagrams illustrating another example of a biosignal detecting apparatus, in accordance with an embodiment.
Figure 8:
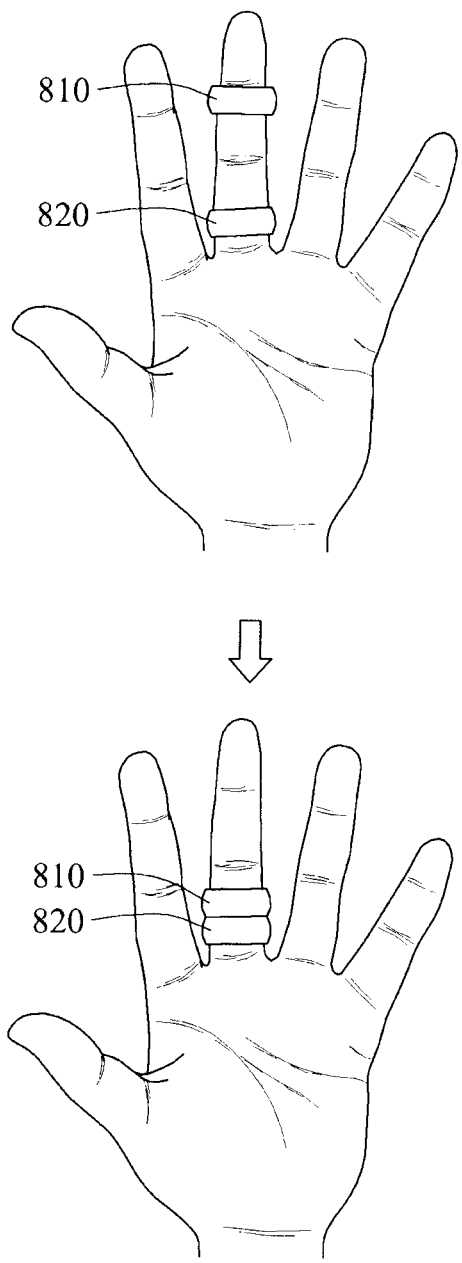

FIGS. 7 and 8 are diagrams illustrating another example of a biosignal detecting apparatus.

Referring to FIG. 7, a configuration of a first body 720 worn on a finger differs from a configuration of a second body 710 worn on another finger. An electrode disposed in an inner surface of the first body 720 is in contact with a middle finger of a user. An electrode disposed along an inner surface of the second body 710 is in contact with an index finger of the user. Each electrode included in a pair of electrodes is disposed in a physically separated ring-type body. When the first body 720 and the second body 710 are not in contact, the biosignal detecting apparatus does not detect a biosignal of the user. When an electrical connection is absent between the first body 720 and the second body 710, the biosignal detecting apparatus does not detect the biosignal of the user.

An outer surface of the first body 720 and an outer surface of the second body 710 include a conductive material. The first body 720 and the second body 710 are in contact in response to a movement of the user. The electrical connection is formed between the first body 720 and the second body 710 in response to the contact. Thus, the biosignal detecting apparatus detects the biosignal, for example, a skin conductance, of the user in response to the formation of the electrical connection.

Referring to FIG. 8, a first body 820 and a second body 810 are worn on a same finger. In one configuration, a positive electrode is disposed along an inner surface of the first body 820, and a negative electrode is disposed along an inner surface of the second body 810. In another configuration, the negative electrode is disposed along the inner surface of the first body 820, and the positive electrode is disposed along the inner surface of the second body 810. Each electrode included in a pair of electrodes is disposed in a physically separated ring-type body.

An electrical connection may not be formed between the first body 820 and the second body 810. Thus, the biosignal detecting apparatus may not detect a biosignal of a user due to an absence of the electrical connection. However, the first body 820 and the second body 810 may be in contact with each other due to a movement of the user. Thus, the electrical connection may be formed between the first body 820 and the second body 810, and the biosignal detecting apparatus may detect the biosignal of the user.

Referring back to FIG. 6, the biosignal detecting apparatus 600 may further include a processor 640, a communication module 650, and an outputter 660. The processor verifies whether a measured value of a biosignal detected by the biosignal detecting apparatus 600 is in a reference range. When the measured value is not within the reference range, the processor 640 controls the biosignal detecting apparatus 600 to apply a physical stimulus to a user. For example, when the measured value is less than the reference range, the biosignal detecting apparatus 600 generates heat through the one of the pair of electrodes 610 in contact with the skin of the user. The skin of the user may then produce sweat due to the generation of the heat from the one of the pair of electrodes 610 and, as a result, the measured value of the biosignal may be included in the reference range. Although the processor is illustrated in FIG. 6 to be external to the first body 620 and the second body 630, in one configuration, the processor 640 may be included in at least one of the first body 620 and the second body 630.

The communication module 650 transmits information about the biosignal detected by the biosignal detecting apparatus 600 to a user terminal through wireless communication. For example, the communication module 650 may include a Bluetooth device or an NFC module. The information about the biosignal may be encoded to be transmitted. Although the communication module 650 is illustrated in FIG. 6 to be external to the first body 620 and the second body 630, in one configuration, the communication module may be included at least one of the first body 620 and the second body 630.

The outputter 660 outputs the information about the biosignal detected by the biosignal detecting apparatus 600. For example, the outputter 660 may include a display visually outputting the biosignal. The display may be provided in a form of a flexible display to be disposed on an outer surface of at least one of the first body 620 and the second body 630. In addition, the outputter 660 may output information indicating whether the biosignal detecting apparatus 600 detects a biosignal. For example, the outputter 660 includes an LED, and informs the user that the biosignal detecting apparatus 600 detects the biosignal using the LED.

Descriptions provided with reference to FIGS. 1 through 5 may be applicable to the foregoing description provided with reference to FIG. 6 and thus, repeated description will be omitted here for brevity.

Figure 9:
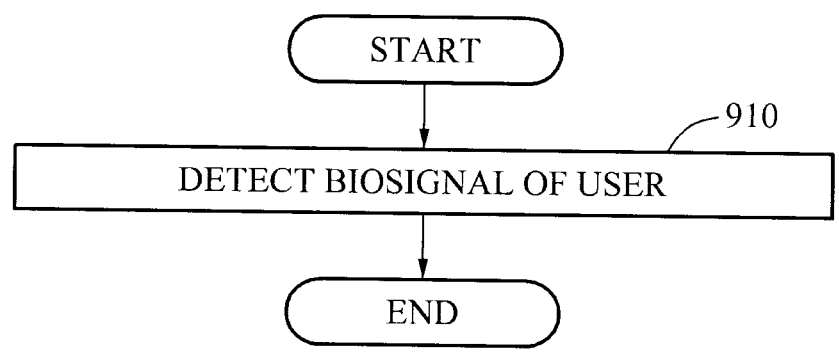
FIG. 9 is a flowchart illustrating an example of a biosignal detecting method, in accordance with an embodiment.

FIG. 9 is a flowchart illustrating an example of a biosignal detecting method, in accordance with an embodiment. The biosignal detecting method to be described hereinafter may be performed by the biosignal detecting apparatus 600.

Referring to FIG. 9, in operation 910, the method detects, through the biosignal detecting apparatus 600, a biosignal of a user. For example, the biosignal detecting apparatus 600 detects a skin conductance of the user. The biosignal detecting apparatus 600 includes a ring-type main body to be worn around a finger of the user. In addition, the biosignal detecting apparatus 600 includes at least one pair of electrodes to be in contact with the finger of the user. At least one electrode included in the pair of electrodes may be disposed in an inner surface of the main body.

The biosignal detecting apparatus 600 may further include a reference unit on an outer surface of the main body to allow a reference position of the biosignal detecting apparatus 600 to be identified. For example, the reference unit may include an ornament, and the ornament may be disposed on the outer surface of the main body. The user may identify the reference position of the biosignal detecting apparatus 600 using the reference unit.

One electrode included in the pair of electrodes may be disposed along one surface of the inner surface between the reference position and an opposite reference position corresponding to the reference position. Another electrode included in the pair of electrodes may be disposed along another surface of the inner surface between the reference position and the opposite reference position.

The at least one pair of electrodes may be alternately disposed along the inner surface of the main body. For example, a positive electrode and a negative electrode may be alternately disposed along the inner surface. In addition, the pair of electrodes may be disposed adjacent to each other along the inner surface of the main body.

One electrode of the pair may be disposed along the inner surface of the main body, and another electrode may be disposed along the outer surface. For example, a positive electrode may be provided in a shape identical to the main body and disposed along the inner surface of the main body. A negative electrode may be disposed along the outer surface of the main body. The negative electrode may cover a portion of the outer surface of the main body. Alternatively, the negative electrode may be provided in a shape identical to the main body to cover all portions of the outer surface of the main body.

The pair of the electrodes may be disposed in the inner surface of the main body. The inner surface of the main body is divided into at least two surfaces based on a baseline formed along the inner surface. One electrode of the pair of electrodes is disposed along one surface of the at least two surfaces of the inner surface, and another electrode is disposed along another surface of the at least two surfaces of the inner surface. Each electrode included in the pair is provided in a type of a ring to allow the electrode to be disposed along the inner surface. The baseline may be formed on the inner surface of the main body to allow the electrodes included in the pair to be separately disposed. For example, a positive electrode is disposed along one surface of the inner surface based on the baseline, and a negative electrode is disposed along another surface of the inner surface based on the baseline.

The biosignal detecting apparatus may further include a ring-type auxiliary body, which is physically separated from the main body. In one example, one electrode of the pair of electrodes is disposed along the inner surface of the main body. Another electrode of the pair of electrodes is disposed along an inner surface of the auxiliary body. When an electrical contact is present between the main body and the auxiliary body, the biosignal detecting apparatus detects a biosignal of the user.

Descriptions provided with reference to FIGS. 1 through 8 may be applicable to the foregoing description provided with reference to FIG. 9 and thus, repeated descriptions will be omitted here for brevity.

Figure 10:
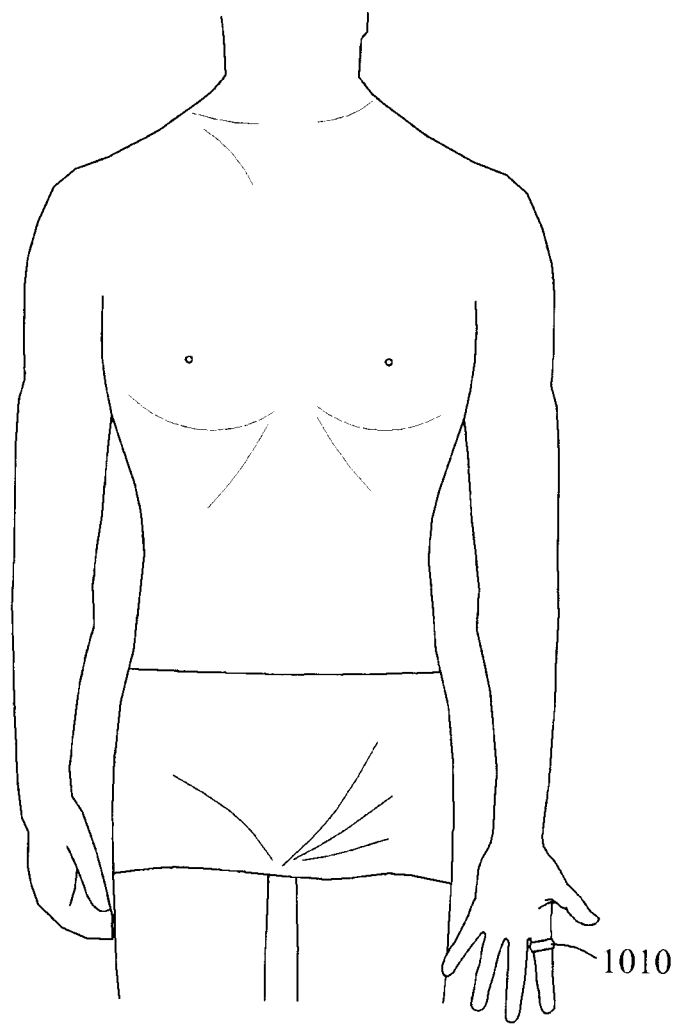
FIG. 10 is a diagram illustrating an application example of the biosignal detecting apparatus, in accordance with an embodiment.

FIG. 10 is a diagram illustrating an application example of the biosignal detecting apparatus, in accordance with an embodiment.

Referring to FIG. 10, a user wears a wearable device 1010. The wearable device 1010 measures a biosignal of the user. For example, the wearable device 1010 is worn around a finger of the user, and measures a skin conductance, a degree of skin hydration, or a degree of skin dryness. The wearable device 1010 may also measure a blood pressure of the user.

An error may occur in a value of a biosignal measured by the wearable device 1010 depending on a position at which the wearable device 1010 is worn. The biosignal is more accurately measured in a palm than in a dorsum of a hand. When a comparison of a case in which an electrode of the wearable device 1010 is in contact with the palm and a case in which the electrode of the wearable device 1010 is in contact with the dorsum is performed, the biosignal is more accurately measured in the former case than in the latter case. The wearable device 1010 adjusts a position of the electrode to minimize the error in the value of the biosignal measured by the wearable device 1010. When the wearable device 1010 moves from the wearing position, a contact area in which the electrode and skin of the user are in contact with each other may be changed. The wearable device 1010 may accurately measure the biosignal by disposing the electrode to minimize or prevent the change.

The wearable device 1010 may include a transmitter. The wearable device 1010 transmits the measured biosignal to a user terminal through the transmitter. For example, the wearable device 1010 transmits the biosignal through a Bluetooth device or an NFC module. The wearable device 1010 encodes the measured biosignal and transmits the biosignal to the user terminal. The wearable device 1010 forms a wireless body area network (WBAN) along with the user terminal.

The wearable device 1010 includes a display. The wearable device 1010 outputs the measured biosignal onto the display. The user verifies the biosignal output on the display. For example, when a measured skin conductance is less than a predetermined value, the wearable device 1010 generates heat in an area of an electrode in contact with the skin of the user. The skin of the user produces sweat in response to the generation of the heat and; as a result, the skin conductance may increase due to the production of sweat. The user verifies a change in the skin conductance output on the display.

Figure 11:
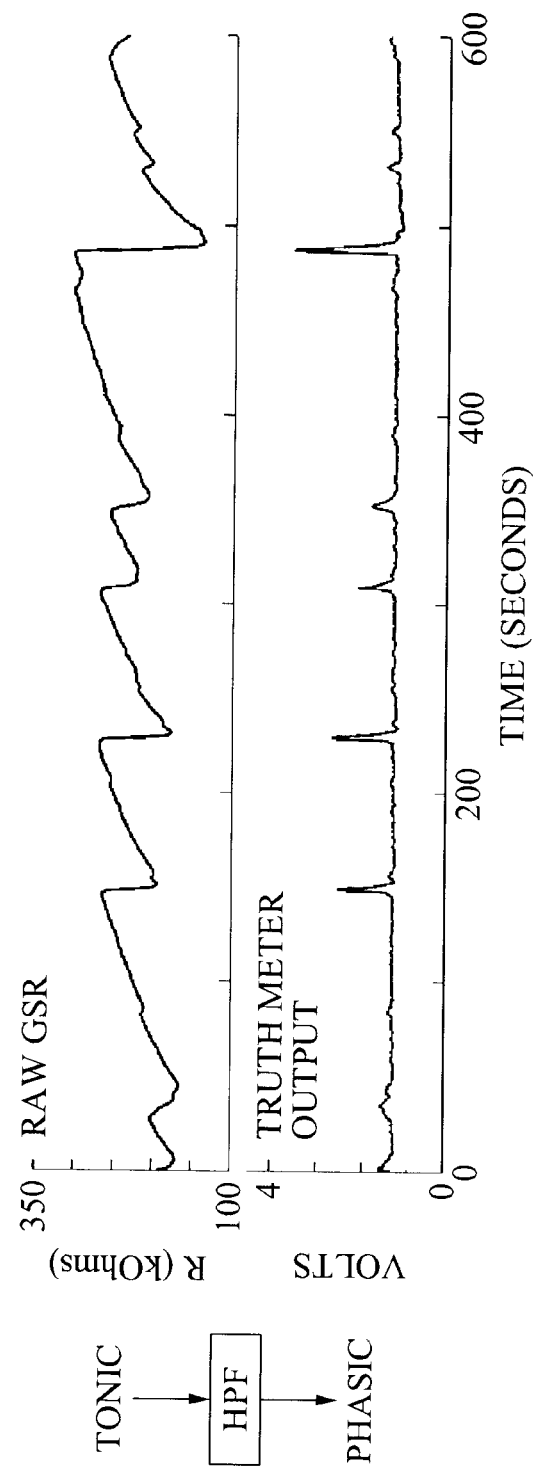
FIG. 11 is a diagram illustrating an example of a biosignal measured by the biosignal detecting apparatus, in accordance with an embodiment.

FIG. 11 is a diagram illustrating an example of a biosignal measured by the biosignal detecting apparatus, in accordance with an embodiment.

Referring to FIG. 11, a raw signal measured by the biosignal detecting apparatus is also referred to as a tonic. A skin conductance illustrated in a first graph indicates the tonic. A y axis of the first graph indicates a resistance, which is an inverse of a galvanic skin response (GSR). At a point, sweat may be produced by a response of sympathetic nerves. Referring to the first graph, the resistance decreases at each point in time at which the sweat is produced.

When the biosignal detecting apparatus filters the tonic using a high-pass filter (HPF), the biosignal detecting apparatus extracts a phasic from the tonic. The tonic is a low-frequency component of a skin conductance, and the phasic is a high-frequency component of the skin conductance. The biosignal detecting apparatus extracts a point in time at which the skin conductance is suddenly changed based on the phasic.

In an example, when the tonic deviates from a predetermined range, the biosignal detecting apparatus performs a predetermined operation to allow the tonic to enter the predetermined range. To analyze a small change in the tonic in the predetermined range, the biosignal detecting apparatus filters the tonic. The biosignal detecting apparatus obtains the phasic from the tonic as a result of the filtering. The biosignal detecting apparatus then verifies the point in time at which the skin conductance suddenly changes based on the phasic.

Provided herein is technology for readily measuring a biosignal of a user. In addition, provided herein is technology to minimize an error in a measured value of a biosignal that may occur depending on a position at which the biosignal is detected.

The units, first body, second body, modules, outputter, and devices described herein may be implemented using hardware components. For example, the hardware components may include controllers, transmitters, receivers, processors, microphones, amplifiers, band-pass filters, audio to digital convertors, and processing devices. A processing device may be implemented using one or more general-purpose or special purpose computers, such as, for example, a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such a parallel processors.

It is to be understood that in the embodiment of the present invention, the operations in FIG. 9 are performed in the sequence and manner as shown although the order of some operations and the like may be changed without departing from the spirit and scope of the described configurations. In accordance with an illustrative example, a computer program embodied on a non-transitory computer-readable medium may also be provided, encoding instructions to perform at least the method described in FIG. 9.

Program instructions to perform a method described in FIG. 9, or one or more operations thereof, may be recorded, stored, or fixed in one or more non-transitory computer-readable storage media. The program instructions may be implemented by a computer. For example, the computer may cause a processor to execute the program instructions. The media may include, alone or in combination with the program instructions, data files, data structures, and the like. Examples of computer-readable media include magnetic media, such as hard disks, floppy disks, and magnetic tape; optical media such as CD ROM disks and DVDs; magneto-optical media, such as optical disks; and hardware devices that are specially configured to store and perform program instructions, such as read-only memory (ROM), random access memory (RAM), flash memory, and the like. Examples of program instructions include machine code, such as produced by a compiler, and files containing higher level code that may be executed by the computer using an interpreter. The program instructions, that is, software, may be distributed over network coupled computer systems so that the software is stored and executed in a distributed fashion. For example, the software and data may be stored by one or more computer readable recording mediums. Also, functional programs, codes, and code segments for accomplishing the example embodiments disclosed herein may be easily construed by programmers skilled in the art to which the embodiments pertain based on and using the flow diagrams and block diagrams of the figures and their corresponding descriptions as provided herein. A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A biosignal detecting apparatus, comprising:
a ring-type main body;
a pair of electrical electrodes configured to be in contact with a finger of a user and to measure a biosignal of the user, wherein
a first electrical electrode of the pair of electrical electrodes is disposed along a first circumferentially extended portion of an inner surface of the ring-type main body, and
a second electrical electrode of the pair of electrical electrodes is disposed along a second circumferentially extended portion of the inner surface of the ring-type main body; and
at least two interfaces configured to prevent a contact between the first electrical electrode of the pair of electrical electrodes and the second electrical electrode of the pair of electrical electrodes, the at least two interfaces being disposed between each end of the pair of electrical electrodes and including respective insulating materials.

2. The apparatus of claim 1, further comprising:
a reference unit disposed on an outer surface of the ring-type main body to allow a reference position of the biosignal detecting apparatus to be identified.

3. The apparatus of claim 2, wherein the reference unit comprises an ornament.

4. The apparatus of claim 2, wherein the first electrical electrode of the pair of electrical electrodes is disposed along one surface of the inner surface between the reference position and another reference position, opposite to the reference position, and
the second electrical electrode of the pair of electrical electrodes is disposed along another surface of the inner surface between the reference position and the another reference position.

5. The apparatus of claim 4, wherein
the reference unit is disposed on the outer surface of the ring-type main body corresponding to at least one of the reference position and the another reference position.

6. The apparatus of claim 1, further comprising:
an outputter configured to output information on the measured biosignal.

7. The apparatus of claim 1, further comprising:
a communicator configured to transmit information about the measured biosignal.

8. The apparatus of claim 1, wherein the biosignal is an electrical conductance of skin.

9. The apparatus of claim 1, wherein the pair of electrical electrodes are spaced apart within the inner surface of the ring-type main body.

10. The apparatus of claim 1, further comprising:
a processor configured to detect and measure the biosignal, and verify whether a measured value of the biosignal detected is in a reference range;
a communication module configured to transmit information about the detected and measured biosignal to a user terminal in response to the measured value being verified; and
an outputter configured to display the information about the detected and measured biosignal.

11. The apparatus of claim 10, wherein, when the measured value is not within the reference range, the processor controls the biosignal detecting apparatus to apply a physical stimulus to a user.

12. The apparatus of claim 1, wherein
the first electrical electrode and the second electrical electrode collectively cover an entire surface of the inner surface of the ring-type main body except for portions of the entire surface of the inner surface where the at least two interfaces being disposed between each end of the pair of electrical electrodes.

* * * * *